United States Patent [19]

Wright

[11] Patent Number: 4,581,349

[45] Date of Patent: Apr. 8, 1986

[54] CERTAIN BENZODIIMIDAZOLES AND THEIR USE AS RADIATION SENSITIZERS

[75] Inventor: Jeremy Wright, Parkton, Md.

[73] Assignee: University of Maryland, Baltimore, Md.

[21] Appl. No.: 622,898

[22] Filed: Jun. 21, 1984

[51] Int. Cl.⁴ .................. A61K 31/675; C07D 487/04
[52] U.S. Cl. ..................................... 514/81; 514/387; 514/388; 514/393; 514/394; 514/395; 548/114; 548/302; 548/305; 548/306; 548/323; 548/326
[58] Field of Search ............... 548/326, 323, 114, 302, 548/305, 306; 514/81, 388, 387, 393, 394, 395

[56] References Cited

U.S. PATENT DOCUMENTS 3,060,188  10/1962  Marxer ................................ 548/326

OTHER PUBLICATIONS

*Chemical Abstracts,* 47:12366g (1952).
[L. S. Efros, *Zhur Obshchei Khim.* 22, 1008–15 (1952)].
A. Marxer, *Helv. Chim. Acta* 44, 762–770 (1961).
E. Winkelmann, *Tetrahedron,* vol. 25, 2427–2454 (1969).

*Primary Examiner*—Richard A. Schwartz
*Attorney, Agent, or Firm*—Elizabeth A. Bellamy; John L. White; I. William Millen

[57] ABSTRACT

This invention relates to novel benzodiimidazole diols and diones and their ability to sensitize hypoxic cells to radiation, thus demonstrating utility for enhancing the treatment of solid tumors by radiation in a subject in need of such treatment.

26 Claims, No Drawings

CERTAIN BENZODIIMIDAZOLES AND THEIR USE AS RADIATION SENSITIZERS

FIELD OF THE INVENTION

This invention relates to novel benzodiimidazoles and their use as radiation sensitizers. More specifically, this invention relates to novel benzo[1,2-d:4,5-d']diimidazole 4,8-diols and 4,8-diones substituted at the 2- and 6-positions and their ability to sensitize hypoxic cells in solid tumors to the action of ionizing radiation, whilst producing minimal undesirable side effects. Thus, there is provided a method for treating humans or other mammalian species suffering from solid tumors.

GENERAL DESCRIPTION OF THE INVENTION COMPOSITION-OF-MATTER ASPECT

In its composition-of-matter aspect this invention relates to novel benzodiimidazoles and their pharmaceutically acceptable salts. Particularly, this invention relates to the novel benzodiimidazole compounds defined by the following Formulae I and II:

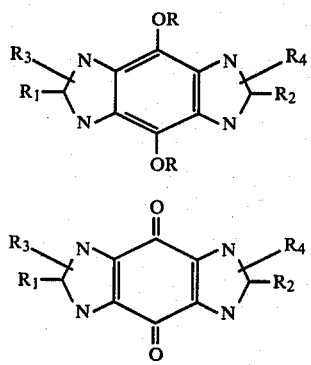

wherein
R is hydrogen, loweralkyl, loweralkanoyl, benzyl, p-methoxybenzyl, $PO_3H$, $SO_3H$;
$R_1$, $R_2$ are independently hydrogen, hydroxy, amino, halogen, haloloweralkyl, dihaloloweralkyl, trihaloloweralkyl, perhaloloweralkyl, cyano, loweralkoxycarbonyl, carbamoyl, substituted carbamoyl wherein the substituents are loweralkyl or hydroxyloweralkyl, sulfamoyl, loweralkanoyl, loweralkylsulfonyl, arylsulfonyl, substituted arylsulfonyl wherein the substituents are hydroxy, halogen, haloloweralkyl, dihaloloweralkyl, trihaloloweralkyl, cyano and loweralkoxycarbonyl, aroyl, substituted aroyl wherein the substituents are hydroxy, amino, halogen, haloloweralkyl, dihaloloweralkyl, trihaloloweralkyl, perhaloloweralkyl, cyano, loweralkoxycarbonyl, sulfamoyl, loweralkanoyl, carbamoyl, or substituted carbamoyl wherein the substituents are loweralkyl or hydroxyloweralkyl;
$R_3$, $R_4$ are hydrogen, loweralkyl, loweralkanoyl, loweralkylaminoalkyl, diloweralkylaminoloweralkyl, benzyl;
----the dotted line represents the presence of a double bond;
with the proviso that $R_1$ and $R_2$ cannot both be hydrogen, hydroxyl or amino groups;
and the pharmaceutically acceptable salts thereof.

In the above formulae, halogen represents fluorine, chlorine, bromine, and iodine. Lower-alkyl/alkoxy/alkanoyl shall refer to a straight or branched chain of from 1 to 4 carbon atoms. The terms aroyl and substituted aroyl shall represent benzoyl or naphthoyl moieties.

Preferred classes of compounds embodied by Formula I are those wherein R, $R_3$ and $R_4$ are as defined for Formula I; $R_1$, $R_2$ are hydrogen, hydroxy, amino, cyano, halogen, haloloweralkyl, dihaloloweralkyl, trihaloloweralkyl, perhaloloweralkyl and loweralkoxycarbonyl; with the proviso that $R_1$ and $R_2$ cannot both be hydrogen, hydroxy or amino.

The more preferred compounds of Formula I are those of the following Formula III:

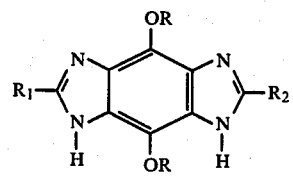

wherein
R is hydrogen or loweralkyl;
$R_1$, $R_2$ are halogen, haloloweralkyl, dihaloloweralkyl, trihaloloweralkyl or perhaloloweralkyl; and
$R_3$ and $R_4$ are hydrogen.

The most preferred compounds of Formula III are those wherein R is hydrogen or loweralkyl and $R_1$ and $R_2$ are trifluoromethyl.

Preferred classes of compounds embodied by Formula II are those wherein $R_3$, $R_4$ are hydrogen or loweralkyl; $R_1$, $R_2$ are hydrogen, hydroxy, amino, cyano, halogen, haloloweralkyl, dihaloloweralkyl, trihaloloweralkyl, perhaloloweralkyl, loweralkanoyl, carbamoyl, sulfamoyl, loweralkylsulfonyl, arylsulfonyl; with the proviso that $R_1$ and $R_2$ cannot both be hydrogen, hydroxy or amino groups.

The more preferred compounds of Formula II are those of the following Formula IV:

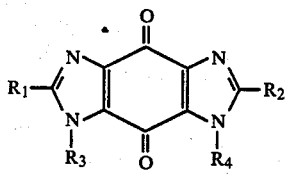

wherein
$R_3$, $R_4$ are hydrogen or loweralkyl;
$R_1$, $R_2$ are hydrogen, hydroxy, amino, cyano, halogen, haloloweralkyl, dihaloloweralkyl, trihaloloweralkyl, perhaloloweralkyl, loweralkanoyl, carbamoyl, sulfamoyl, loweralkylsulfonyl, arylsulfonyl;
with the proviso that $R_1$ and $R_2$ cannot both be hydrogen, hydroxy or amino groups.

Still more preferred compounds are those of Formula IV wherein $R_1$ and $R_2$ are as defined therein and wherein $R_3$ and $R_4$ are both hydrogen.

Most preferred compounds are those of Formula IV wherein $R_1$ is hydrogen or $R_2$ wherein $R_2$ is trihaloloweralkyl; and $R_3$ and $R_4$ are hydrogen.

It will be obvious from Formulae I and II that the ----dotted line which indicates the presence of a double bond may be in one of several positions. Thus, tautomeric isomers are possible and any and all such isomers are deemed to be part of the scope of the present invention. Illustrative and most preferred of the class of tautomers are those of the Formula V:

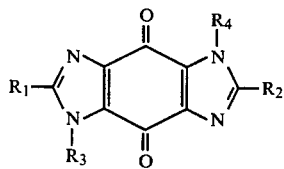

wherein $R_1$, $R_2$, $R_3$ and $R_4$ are as defined for Formula IV.

The compounds which follow are some of those which serve to exemplify various aspects of the invention described herein.
(1) 4,8-Dihydroxybenzo[1,2-d:4,5-d']-2,6-bis-trifluoromethyldiimidazole
(2) 4,8-Dimethoxybenzo[1,2-d:4,5-d']-2,6-bis-trifluoromethyldiimidazole
(3) 2,6-bis-Trifluoromethylbenzo[1,2-d:4,5-d']diimidazole-4,8-dione
(4) 2-Trifluoromethylbenzo[1,2-d:4,5-d']diimidazole-4,8-dione
(5) 2-trifluoromethyl-6-aminobenzo[1,2-d:4,5-d']diimidazole-4,8-dione
(6) 2,6-bis-Pentafluoroethylbenzo[1,2-d:4,5-d']diimidazole-4,8-dione
(7) 2,6-bis-Heptafluoropropylbenzo[1,2-d:4,5-d']diimidazole-4,8-dione
(8) 2,6-Dicyanobenzo[1,2-d:4,5-d']diimidazole-4,8-dione
(9) 2,6-bis-Methanesulfonylbenzo[1,2-d:4,5-d']diimidazole-4,8-dione
(10) 2,6-bis-Sulfamoylbenzo[1,2-d:4,5-d']diimidazole-4,8-dione
(11) 2,6-bis-Carbamoylbenzo[1,2-d:4,5-d']diimidazole-4,8-dione
(12) 2-Trifluoromethyl-6-carbamoylbenzo[1,2-d:4,5-d']diimidazole-4,8-dione
(13) 1-Benzyl-2,6-bis-trifluoromethylbenzo[1,2-d:4,5-d']diimidazole-4,8-dione
(14) 1-Methyl-2,6-bis-trifluoromethylbenzo[1,2-d:4,5-d']diimidazole-4,8-dione
(15) 2,6-bis-Pentafluorobenzoylbenzo[1,2-d:4,5-d']diimidazole-4,8-dione Also contemplated as part of this invention are the pharmaceutically acceptable salts of the compounds of Formulae I and II. When one or several of $R_1$, $R_3$ and $R_4$ are H, the resultant compound will be acidic and thus form salts with inorganic and organic bases. Such bases are selected from, but not limited to, sodium, potassium, triethylamine, meglumine, ethylenediamine, and guanidine. It will be obvious to those skilled in the art that the degree of acidity of the parent compound will determine which inorganic or organic base to use.

It is expected that the compounds of Formulae I or II wherein the $R_1$, $R_2$ positions contain the nitro or dicyanovinyl groups, would be active within the definition of this invention.

PROCESS ASPECT

In general, the compounds of this invention may be prepared by various processes and reactants known in the art. In order to produce the compounds of Formulae I and II and intermediates thereto, the following Schemes A and B are most usually employed.

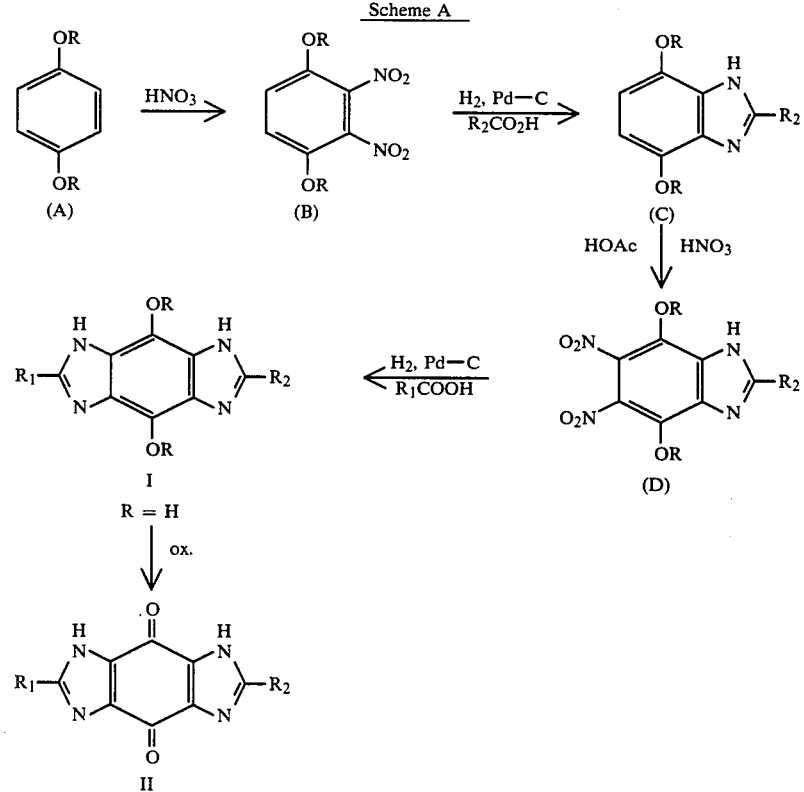

Scheme A

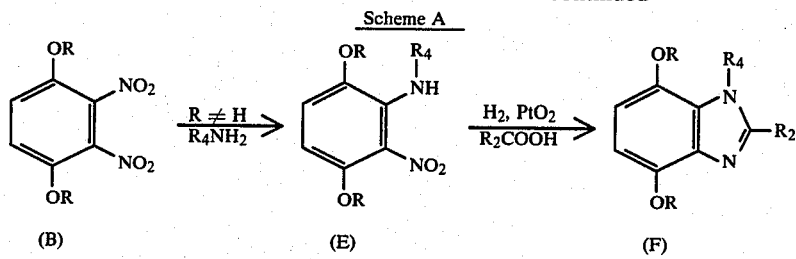

In Scheme A, a diether of 1,4-dihydroxybenzene, loweralkyl or preferably dibenzyl is nitrated first with concentrated nitric acid to a mononitro derivative and then with fuming nitric acid in glacial acetic acid at or below 0° C. to give a mixture of 2,3- and 2,5-dinitro derivatives. Reaction of this mixture with an amine $R_4NH_2$ in a refluxing loweralkanol selectively forms 2-substituted amino-3-nitro-1,4-benzenedioldiether (E), leaving the insoluble 2,5-dinitroisomer unchanged.

Compound E can be selectively hydrogenated in the presence of a platinum oxide catalyst and a carboxylic acid $R_2COOH$ to the N-substituted benzimidazole Compound F. If $R_4$ is a benzyl group it will not be removed. If however, the hydrogenolysis takes place in the presence of palladium/carbon (10%) the benzyl group will be cleaved, so that in compound F, $R_4$ will be hydrogen.

Compound F can be nitrated with fuming nitric acid in glacial acetic acid at 0° C. to 20° C. to give the dinitro intermediate Compound D where $R_4$ is optionally not hydrogen.

Hydrogenation of Compound D in the presence of $R_1COOH$, or optionally in loweralkanol solvent affords directly Compound I or a 5,6-diamino intermediate respectively. This latter 5,6-diamino intermediate can be condensed to a benzodiimidazole in the presence of carbonic acid or carboxylic acid $R_1COOH$ derivatives. For example, condensation of the 5,6-diamino intermediate with cyanogen bromide will give Compound I wherein $R_1=NH_2$ and with phosgene, Compound I wherein $R_1=OH$.

Compounds I wherein R is benzyl may be further hydrogenated in mineral acid at temperatures above 50° C. in the presence of platinum or palladium catalysts to the dihydroxy Compounds I (R=H). These compounds may be oxidized with iron or chromium reagents to the diones compound II.

Scheme B

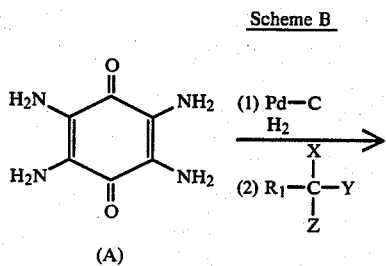

wherein in certain instances
X, Y = O; Z = OH
$R_1 = X = Y = SR'$; Z = halide
wherein R' = loweralkyl or phenyl
X, Y, Z also = OR'

-continued
Scheme B

I (R = $R_3$ = $R_4$ = H)
($R_1$ = SR')

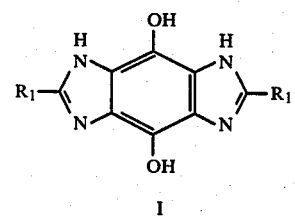

II ($R_1$ = —$SO_2R'$)

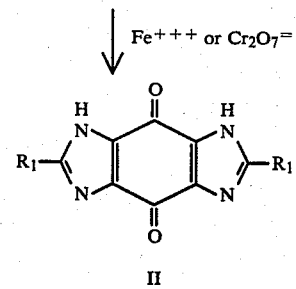

I

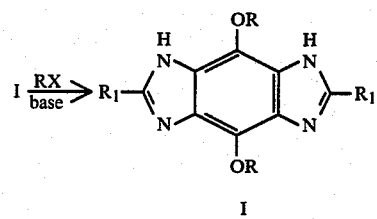

II

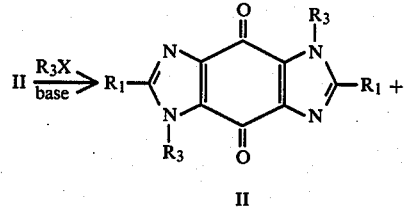

II

As illustrated by the foregoing Scheme B symmetrical compounds of the present invention ($R_1=R_2$) may be produced. The tetraaminobenzoquinone is preferably reduced with hydrogen in the presence of a noble metal catalyst to the diol Compound I which is condensed various carbonic, thiocarbonyl and carboxylic acids to provide benzodiimidazoles I.

In the case that the condensing reagent is carbon disulfide the intermediate I ($R_1=SH$) may be oxidized with chlorine to I ($R_1=SO_2Cl$) which is then reacted with ammonia or amines to produce I ($R_1=$sulfamoyl or N-substituted sulfamoyl). Optionally I ($R_1=SH$) may be alkylated and the resulting bis-2-alkylthiobenzodiimidazoles oxidized with reagents known in the art to I ($R_1=O_2SR$) wherein the substituents $R_1=O_2SR$ conform to the above defined $R_1$.

In the case of the condensation of the tetraamine intermediate A with formic acid, the resulting benzodiimidazole wherein $R_1=H$ can be substituted in the 2,6-positions using acylating reagents known in the art such as chlorosulfonylisocyanate, to produce Compounds I wherein $R_1$ is an acyl or benzoyl or carbamoyl substituent conforming to the above definition.

Alkylation of Compound II is accomplished (in the $R_1$ positions when $R_1$ is H and $R_3$ is H) with loweralkyl halides, benzyl halides, loweralkylaminoalkyl halides or N,N-diloweralkylaminoalkyl halides.

METHOD-OF-USE AND PHARMACEUTICAL COMPOSITION ASPECT

The novel benzodiimidazoles of this invention have been found to sensitize hypoxic cells to the action of ionizing radiation with minimal undesirable side effects. This property is found to be useful in the use of ionizing radiation for the treatment of subjects suffering from illness caused by solid cell tumors.

It has long been established that poorly vascularized solid tumors contain a region of cells which exist in an environment of low oxygen tension. Since the presence of oxygen is necessary to produce the maximum effect in radiation therapy, these hypoxic cells are resistant to the effects of radiation and, in point of fact, serve as a focus for tumor regrowth.

One approach to deterring tumor regrowth has been to develop compounds which penetrate into the hypoxic cell region of the solid tumor and their mimic the effects of oxygen whereby the radiation treatment then becomes much more effective. Compounds which have been found to penetrate the hypoxic cell region include derivatives of the nitroimidazoles, e.g. metronidazole (Flagyl®) and misonidazole. However, these nitroimidazoles, albeit potent hypoxic cell radiosensitizers, are limited in their use by the neurotoxic symptoms they produce at therapeutic levels. Thus, it appears these nitro group containing compounds cross the blood-brain barrier swiftly enough to cause the neurotoxic symptoms before they are eliminated.

The approach of this invention is to provide novel benzodiimidazoles containing electron affinic groups other than nitro which are potent non-toxic radiosensitizing agents.

These benzodiimidazoles have been tested in in vitro and in vivo models. The prelimiary radiation studies were performed with these compounds versus *Serratia marsescens,* the secondary studies were performed by measuring radiosensitizing activity against implanted tumors in mice. Both methods are explained in detail in the article Wright, Harrison et al. Radiation Research 95, 187–196 (1983).

Compounds of the present invention exemplified by 4,8-dihydroxybenzo[1,2-d:4,5-d']-2,6-trifluoromethyldiimidazole and benzo[1,2-d:4,5-d']-2,6-trifluoromethyldiimidazole-4,8-quinone proved to be potent radiosensitizing agents. Additionally, when administered at a single dose of 200 mg/kg i.p. to a rat they displayed none of the toxic effects which are typical of the prior art nitroimidazoles. Still further, daily injections of 100 mg/kg/day to five mice for two months elicited no untoward signs of toxicity or loss of body weight. Thus, it is evident that the compounds of this invention enhance the therapeutic effect of radiation in a subject in need of such radiation treatment, without the concurrent neuro-toxic symptoms of the prior art compounds.

The compounds of this invention when admixed with a non-toxic pharmaceutically acceptable carrier provide a pharmaceutical composition for enhancing the therapeutic effect of radiation. These pharmaceutical compositions, as for instance, one with benzo[1,2-d:4,5-d']-2,6-trifluoromethyldiimidazole-4,8-dione admixed with a non-toxic pharmaceutically acceptable carrier, are administered orally or parenterally, and preferably intravenously. The dose employed will be dependent on the radiation protocol necessary for each subject. In protocols where the radiation dose is divided into a large number of fractions, the drug can be administered at intervals in the schedule and not necessarily with each radiation treatment. It should be noted that the compounds of the present invention can be used for acute and chronic administration. In general, the drug is administered from from 10 minutes to 4 hours prior to the radiation treatment in a dosage amount of between 0.05 to about 4.0 grams per square meter of body surface approximately equivalent to a dosage of 1.25 to 100 mg/kg of subject body weight. The dose for the individual subject may begin with an initial dose of 0.05 gm/square meter of body surface to determine how well the drug is tolerated and then increasing the dosage with each succeeding radiation treatment, observing the subject carefully for any drug side effect.

The dosage form from intravenous administration is a sterile isotonic solution of the drug. Oral dosage forms such as tablets, capsules, or elixirs are preferred. Capsules or tablets containing from 10, 25, 50, 100 or 250 mg of drug/capsule or tablet are satisfactory for use in the method of treatment of our invention. For tablets or capsules the substantially pure compound may be combined with a pharmaceutically acceptable solid diluent or in the case of capsules, filled directly into an appropriately sized capsule.

The invention described hereinabove is illustrated below in the Preparations and Examples, which, however, is not to be construed as limiting the scope of this invention.

PREPARATIONS

Preparation 1

2-Nitro-1,4-dimethoxybenzene

To a mixture of 100 ml concentrated nitric acid and 200 ml water is added 34.20 (0.30 mole) 1,4-dimethoxybenzene over a period of half an hour. After an additional fifteen minutes of stirring, the mixture is poured over ice. The resulting crystals are collected by filtration and crystallized from ethanol yielding bright yellow needles with a melting point of 68°–70° C.

Preparation 2

Dinitro-1,4-dimethoxybenzene

2-Nitro-1,4-dimethoxybenzene (3.30 g, 0.014 mole) is added in portions to a mixture of equal parts of fuming nitric and glacial acetic acids while keeping the temperature at or below 0° C. After thirty minutes of stirring, the mixture is isolated by filtration, washed with water and dried. The pale yellow needles melt slowly between 155°–170° C. This product contains an equal mixture of the 2,3-dinitro and 2,5-dinitro isomers.

Preparation 3

2-Benzylamino-3-nitro-1,4-dimethoxybenzene

A mixture of benzylamine (27.80 g, 0.26 mole) and the isometric dinitrodimethoxy mixture obtained in Preparation 2 (60.0 g, 0.26 mole) is suspended in 500 ml of n-propanol. The mixture is allowed to reflux overnight. On cooling, 2,5-dinitro-1,4-dimethoxybenzene precipitates and is removed by filtration. Upon refrigeration 2-benzylamino-3-nitro-1,4-dimethoxybenzene crystallizes and is isolated by filtration. The orange prisms melt at 60°–62° C.

Preparation 4

2-Amino-1-benzyl-4,7-dimethoxybenzimidazole

2-Benzylamino-3-nitro-1,4-dimethoxybenzene (10.0 g, 0.03 mole) is suspended in methanol and hydrogenated in the presence of platinum oxide catalyst at 50 psi for about twelve hours. After this time the solution changes color from red to colorless. The methanol is then removed in vacuo. To the residue is added approximately 250 ml water and 3.50 g (0.03 mole) of cyanogen bromide. The flask containing this mixture is stoppered, shaken, and stirred overnight at room temperature. After treatment with activated charcoal, the solution is filtered into excess 1N NaOH, causing the precipitation of the product. The amorphous white powder melts at 191°–193° C.

Preparation 5

2-Amino-4,7-dimethoxybenzimidazole

1-Benzyl-2-amino-4,7-dimethoxybenzimidazole (17.85 g, 0.06 mole) is hydrogenated in the presence of palladium on carbon catalyst (10%) at 50 psi for about twelve hours. After filtration the methanol is removed in vacuo and the residue dissolved in boiling water and treated with decolorizing charcoal. The suspension is filtered into 1N NaOH, giving a white precipitate of 2-amino-4,7-dimethoxybenzimidazole. The amorphous white powder melts at 251°–253° C.

Preparation 6

2-Amino-5,6-dinitro-4,7-dimethoxybenzimidazole

2-Amino-4,7-dimethoxybenzimidazole (9.65 g, 0.05 mole) is added in portions to a mixture of equal parts of fuming nitric and glacial acetic acids while keeping the temperature at or below 0° C. After about thirty minutes of stirring the reaction mixture is poured slowly into ice water. The precipitate is collected by filtration, washed with water and dried. The bright yellow needles melt at about 170°–173° C.

NMR: 4.33 (s, 4–7 OCH$_3$).

Preparation 7

2-Hydroxy-4,7-dimethoxybenzimidazole

A methanolic solution of the 2,3-dinitro-4,7-dimethoxybenzene (11.40 g, 0.05 mole) is hydrogenated in the presence of palladium on carbon catalyst (10%) at 50 psi for two hours at room temperature. The catalyst is removed by filtration and the methanol removed in vacuo. The oily residue is refluxed with 100 ml benzene containing 10% phosgene for four days. The solution is then poured into dilute NH$_4$OH, and the resulting crystals isolated by filtration. The yield of amorphous white powder is 9.22 g (95%) with a melting point of >350° C.

Preparation 8

2-Trifluoromethyl-4,7-dimethoxybenzimidazole

An amount of 2,3-dinitro-4,7-dimethoxybenzene (11.40 g, 0.05 mole) suspended in 150 ml trifluoroacetic acid is hydrogenated in the presence of palladium on carbon catalyst (10%) at 50 psi for twenty-four hours. The solution is then filtered into 1N NH$_4$OH and the crystals collected by filtration. The yield of microcrystalline gray solid (after crystallization from trifluoroacetic acid) is 11.07 g (90%) with a melting point of 212°–214° C.

NMR: 3.96 (s,, 4–7 OCH$_3$); 6.80 (s, 5–6 H)

IR (KBr): 3300 cm$^{-1}$ m (NH stretch), 1520 cm$^{-1}$ s, 1440 cm$^{-1}$ s (CC double bond characteristic of benzimidazoles[30]), 1275 cm$^{-1}$ s (CF stretch), 1180 cm$^{-1}$ s (CO bend), 1145 cm$^{-1}$ s (CC stretch).

Preparation 9

2-Trifluoromethyl-5,6-dinitro-4,7-dimethoxybenzimidazole

To a mixture of 125 ml fuming nitric acid and 125 ml glacial acetic acid at −10° C. is added 12.30 g (0.05 mole) 2-trifluoromethyl-4,7-dimethoxybenzimidazole in portions such that the reaction mixture temperature remains below 0° C. After the addition is complete, the reaction mixture is poured slowly over ice and the crystals isolated by filtration. The yellow needles (after crystallization from trifluoroacetic acid) melts at about 208°–210° C.

NMR: 4.23 (s, 4–7 OCH$_3$)

Preparation 10

Tetraphthalimido-1,4-benzoquinone

A suspension of chloranil (10.00 g, 0.04 mole) and potassium phthalimide (30.00 g, 0.16 mole) in acetonitrile is refluxed overnight. The deep purple solution is allowed to cool and then filtered, yielding a tan solid. This solid is then boiled in approximately 200 ml of dimethylformamide for ten minutes. The hot DMF suspension is then filtered yielding a white thixotropic solid.

Preparation 11

Tetraamino-1,4-benzoquinone

Tetraphthalimido-1,4-benzoquinone (30.00 g, 0.044 mole) is added to 200 ml of 80% hydrazine hydrate. The mixture is heated to 60° C. for two hours. After cooling to room temperature, the mixture is filtered yielding dark purple crystals melting at 260°–262° C.

EXAMPLES

Example I 4,8-Dimethoxybenzo[1,2-d:4,5-d']-2,6-trifluoromethyl-diimidazole

2-Trifluoromethyl-5,6-dinitro-4,7-dimethoxybenzimidazole (6.72 g, 0.02 mole) suspended in 150 ml of trifluoroacetic acid is hydrogenated in the presence of palladium on carbon catalyst (10%) at 50 psi for about twenty-four hours. The solution is then filtered into 1N $NH_4OH$ and the crystals collected by filtration. The microcrystalline white solid (after crystallization from trifluoroacetic acid) melts at 363°–365° C. dec.

NMR: 4.33 (s, 4–7 $OCH_3$)

IR (KBr): 1540 $cm^{-1}$ m, 1460 $cm^{-1}$ s, 1410 $cm^{-1}$ (characteristic of benzimidazoles[30]), 1280 $cm^{-1}$ s (CF stretch), 1160 $cm^{-1}$ s (CO bend and CC stretch).

Example II 4,8-Dihydroxybenzo[1,2-d:4,5-d']-2,6-trifluoromethyl-diimidazole

Tetraamino-1,4-benzoquinone (2.10 g, 0.012 mole) in 100 ml of trifluoroacetic acid is hydrogenated in the presence of palladium on carbon catalyst (10%) for a period of four days at 50 psi. The reaction mixture is filtered and the filtrate is then made alkaline by the addition of 1N NaOH. The resultant suspension is filtered, and to the filtrate is added 1N HCl until the product, 4,8-dihydroxybenzo[1,2-d:4,5-d']-2,6-trifluoromethyldiimidazole, is precipitated. The pale yellow needles (after crystallization from glacial acetic acid) melt at >375° C.

IR (KBr): 3400 $cm^{-1}$ w (NH stretch), 1680 $cm^{-1}$ s (CN imidazole double bond[30]), 1550 $cm^{-1}$ m, 1460 $cm^{-1}$ s, 1430 $cm^{-1}$ s (characteristic of benzimidazoles[30]), 1300 $cm^{-1}$ s (CF stretch), 1160 $cm^{-1}$ s (CO bend and CC stretch).

Example III

Benzo[1,2-d:4,5-d']-2,6-trifluoromethyldiimidazole-4,8-quinone 4,8-Dihydroxybenzo[1,2-d:4,5-d']-2,6-trifluoromethyldiimidazole (3.00 g, 0.009 mole) is added to a solution of 3.0 g ferric chloride in 100 ml 50% aqueous acetone. This mixture is heated to 50° C. for one hour and the acetone is removed in vacuo. The aqueous suspension is then made alkaline by the addition of 1N NaOH and filtered. The filtrate is acidified with 1N HCl causing the precipitation of product. The bright yellow needles (after crystallization from ethanol) melt at >375° C.

IR (KBr): 3400 $cm^{-1}$ w (NH stretch), 1690 $cm^{-1}$ s (CO double bond, isolated), 1670 $cm^{-1}$ s (CO double bond, conjugated), 1610 $cm^{-1}$ s (CC double bond), 1300 $cm^{-1}$ s (CF stretch), 1260 $cm^{-1}$ s (CC stretch).

Example IV 4,8-Dimethoxybenzo[1,2-d:4,5-d']-2-trifluoromethyl-6-pentafluoroethyldiimidazole Suspend 2-trifluoromethyl-5,6-dinitro-4,7-dimethoxybenzimidazole (6.72 g, 0.02 mole) in 150 ml of pentafluoropropionic acid. Add 10% palladium on carbon (0.6 g) and hydrogenate at 50 psi, 25° C. for 24 hours. Concentrate the solution under vacuum and add the filtered residue to excess 1N aqueous ammonia. Filter the white, crystalline, title compound.

Example V 4,8-Dihydroxybenzo[1,2-d:4,5-d']-2-trifluoromethyl-6-pentafluoroethyldiimidazole Dissolve the product from Example IV in 200 ml of methylene chloride and add trimethylsilyl iodide (8.0 g, 0.04 mole) and reflux the mixture 18 hours. Concentrate the mixture under vacuum and stir the residue with 9:1 water-methanol for 18 hours. Filter the crystalline title compound, oxidize the resultant product according to the ferric chloride procedure of Example III.

Example VI

2-Amino-6-trifluoromethyl-4,8-dimethoxybenzo[1,2-d:4,5-d']diimidazole

Hydrogenate the title compound from Preparation 6 in 200 ml of trifluoroacetic acid in the presence of 1 g of 10% palladium on carbon at 50 psi and 25° C. for 24 hours. Concentrate the mixture under vacuum and add the filtered solution to excess 1N aqueous ammonia, filter the title compound.

Example VII

2-Amino-6-trifluoromethyl-4,8-dihydroxybenzo[1,2-d:4,5-d']diimidazole

Demethylate the product of Example VI with trimethylsilyl iodide as per the procedure of Example V and isolate the title compound.

Example VIII

2-Amino-6-trifluoromethylbenzo[1,2-d:4,5-d']diimidazole-4,8-dione

Oxidize the product of Example VII according to the ferric chloride procedure of Example III and isolate the title compound.

I claim:

1. A compound of one of the following formulae:

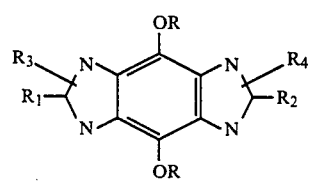

I

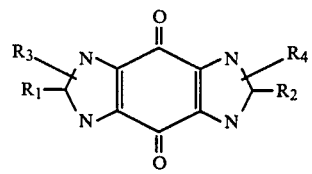

II wherein
R is hydrogen, $PO_3H$, $SO_3H$, benzyl, p-methoxybenzyl, loweralkyl, loweralkanoyl;
$R_1$, $R_2$ are hydrogen, hydroxy, amino, halogen, haloloweralkyl, dihaloloweralkyl, trihaloloweralkyl, perhaloloweralkyl, cyano, loweralkoxycarbonyl, carbamoyl, substituted carbamoyl wherein the substituents are loweralkyl or hydroxyloweralkyl, sulfamoyl, loweralkanoyl, loweralkylsulfonyl, phenylsulfonyl, substituted phenylsulfonyl wherein the substituents are hydroxy, halogen, haloloweralkyl, dihaloloweralkyl, trihaloloweralkyl, cyano and loweralkoxycarbonyl, benzoyl or naphthoyl, substituted benzoyl or naphthoyl wherein the substituents are hydroxy, amino, halogen, haloloweralkyl, dihaloloweralkyl, trihaloloweralkyl, cyano, loweralkoxycarbonyl, sulfamoyl, loweralkanoyl, carbamoyl or substituted carbamoyl wherein the substituents are loweralkyl or hydroxyloweralkyl;

R$_3$, R$_4$ are hydrogen, loweralkyl, loweralkanoyl, loweralkylaminoalkyl, diloweralkylaminoloweralkyl, benzyl;

--the dotted line represents the presence of a double bond;

with the proviso that R$_1$ and R$_2$ cannot both be hydrogen, hydroxyl or amino groups;

or a pharmaceutically acceptable salt thereof.

2. A compound of Formula I, claim 1, wherein R$_1$ and R$_2$ are hydrogen, hydroxy, amino, cyano, halogen, haloloweralkyl, dihaloloweralkyl, trihaloloweralkyl, perhaloloweralkyl, loweralkoxycarbonyl; with the proviso that R$_1$ and R$_2$ cannot both be hydrogen, hydroxy, or amino.

3. A compound of claim 2 of the formula

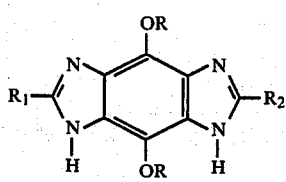

wherein
R is hydrogen or loweralkyl;
R$_1$ and R$_2$ are halogen, haloloweralkyl, dihaloloweralkyl, trihaloloweralkyl or perhaloloweralkyl.

4. A compound of claim 3 wherein R$_1$ and R$_2$ are trifluoromethyl.

5. A compound of claim 4 which is 4,8-dihydroxybenzo[1,2-d:4,5-d']-2,6-bis-trifluoromethyldiimidazole.

6. A compound of claim 4 which is 4,8-dimethoxybenzo[1,2-d:4,5-d']-2,6-bis-trifluoromethyldiimidazole.

7. A compound of Formula II, claim 1, wherein R$_3$, R$_4$ are hydrogen or loweralkyl; R$_1$, R$_2$ are hydrogen, hydroxy, amino, cyano, halogen, haloloweralkyl, dihaloloweralkyl, trihaloloweralkyl, perhaloloweralkyl, loweralkanoyl, carbamoyl, sulfamoyl, loweralkylsulfonyl, phenylsulfonyl; with the proviso that R$_1$ and R$_2$ cannot be hydrogen, hydroxy or amino groups.

8. A compound of claim 7 of the formula

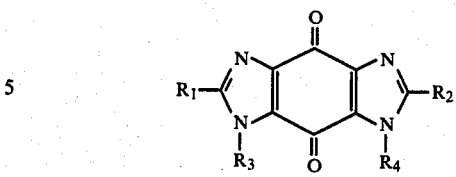

wherein R$_1$, R$_2$, R$_3$ and R$_4$ are as defined therein.

9. A compound of claim 8 wherein R$_3$ and R$_4$ are hydrogen.

10. A compound of claim 9 wherein R$_1$ is hydrogen or R$_2$ wherein R$_2$ is trihaloloweralkyl.

11. A compound of claim 7 of the formula

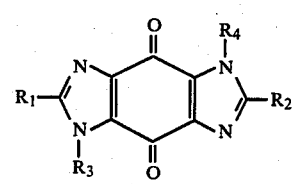

wherein R$_1$, R$_2$, R$_3$ and R$_4$ are defined as therein.

12. A compound of claim 10 which is 2,6-bis-trifluoromethylbenzo[1,2-d:4,5-d']diimidazole-4,8-dione.

13. A compound of claim 10 which is 2-trifluoromethylbenzo[1,2-d:4,5-d']diimidazole-4,8-dione.

14. A compound of claim 9 which is 2-trifluoromethyl-6-aminobenzo[1,2-d:4,5-d']diimidazole-4,8-dione.

15. A compound of claim 9 which is 2,6-bis-pentafluoroethylbenzo[1,2-d:4,5-d']diimidazole-4,8-dione.

16. A compound of claim 9 which is 2,6-bis-heptafluoropropylbenzo[1,2:4,5-d']diimidazole-4,8-dione.

17. A compound of claim 9 which is 2,6-dicyanobenzo[1,2-d:4,5-d']diimidazole-4,8-dione.

18. A compound of claim 9 which is 2,6-bis-methanesulfonylbenzo[1,2-d:4,5-d']diimidazole-4,8-dione.

19. A compound of claim 9 which is 2,6-bis-sulfamoylbenzo[1,2-d:4,5-d']diimidazole-4,8-dione.

20. A compound of claim 9 which is 2,6-bis-carbamoylbenzo[1,2-d:4,5-d']diimidazole-4,8-dione.

21. A compound of claim 9 which is 2-trifluoromethyl-6-carbamoylbenzo[1,2-d:4,5-d']diimidazole-4,8-dione.

22. A compound of claim 8 which is 1-benzyl-2,6-bis-trifluoromethylbenzo[1,2-d:4,5-d']diimidazole-4,8-dione.

23. A compound of claim 8 which is 1-methyl-2,6-bis-trifluoromethylbenzo[1,2-d:4,5-d']diimidazole-4,8-dione.

24. A compound of claim 1 which is 2,6-bis-pentafluorobenzoylbenzo[1,2-d:4,5-d']diimidazole-4,8-dione.

25. A method for enhancing the therapeutic effect of radiation treatment which comprises administering to a subject in need of such radiation treatment an effective radiation sensitizing amount of a compound of claim 1.

26. A pharmaceutical composition for enhancing the therapeutic effect of radiation treatment which comprises an effective amount of radiation sensitizing compound of claim 1 in admixture with a non-toxic pharmaceutically acceptable carrier.

* * * * *

UNITED STATES PATENT AND TRADEMARK OFFICE
CERTIFICATE OF CORRECTION

PATENT NO. : 4,581,349

DATED : April 8, 1986

INVENTOR(S) : Jeremy Wright

Page 1 of 2

It is certified that error appears in the above-identified patent and that said Letters Patent is hereby corrected as shown below:

Column 1, lines 23-30

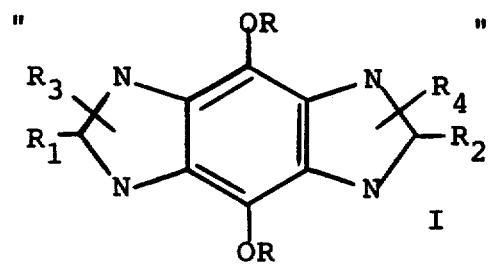 should read 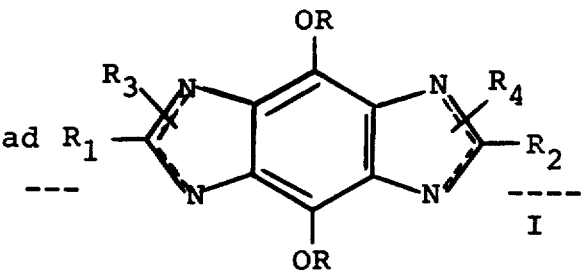

Column 1, lines 31-38

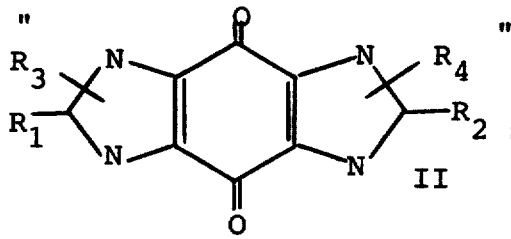 should read 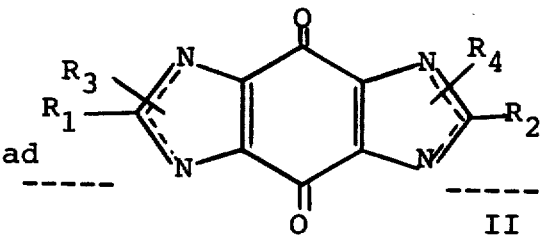

Column 8, line 43 "from" should read --for--.

Column 12, lines 41-48

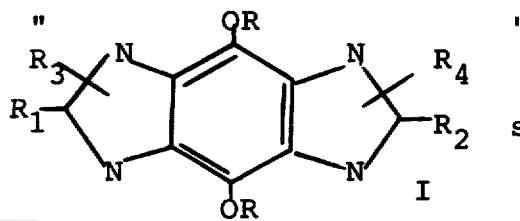 should read 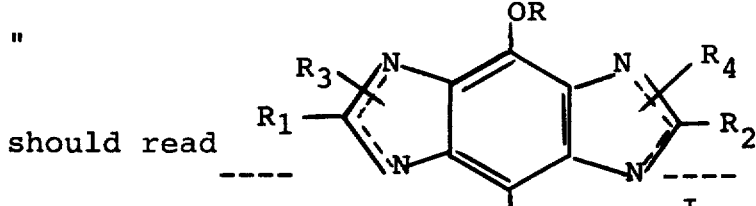

UNITED STATES PATENT AND TRADEMARK OFFICE
CERTIFICATE OF CORRECTION

PATENT NO. : 4,581,349

DATED : April 8, 1986

INVENTOR(S) : Jeremy Wright

Page 2 of 2

It is certified that error appears in the above-identified patent and that said Letters Patent is hereby corrected as shown below:

Column 12, lines 50-56

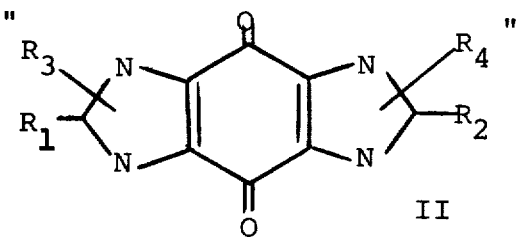 should read 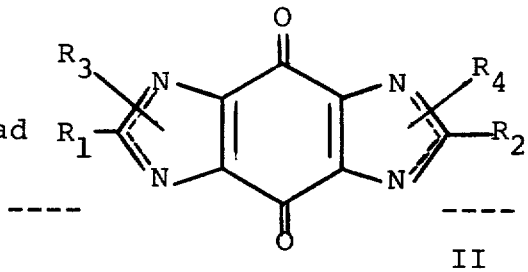

Column 13, line 63, after the "cannot" should read
--cannot both--.

Signed and Sealed this

*Nineteenth* Day of *August 1986*

[SEAL]

*Attest:*

*Attesting Officer*

DONALD J. QUIGG

*Commissioner of Patents and Trademarks*